US008076268B2

(12) United States Patent
Schnabel et al.

(10) Patent No.: US 8,076,268 B2
(45) Date of Patent: Dec. 13, 2011

(54) LIQUID FORMULATIONS CONTAINING DIALKYL SULFOSUCCINATE AND HYDROXYPHENYLPYRUVATE DIOXYGENASE INHIBITORS

(75) Inventors: Gerhard Schnabel, Elsenfeld (DE); Detlev Haase, Frankfurt (DE); Gerhard Frisch, Wehrheim (DE); Martin Bommel, Sulzbach (DE)

(73) Assignee: Bayer CropScience AG, Monheim (DE)

( * ) Notice: Subject to any disclaimer, the term of this patent is extended or adjusted under 35 U.S.C. 154(b) by 610 days.

(21) Appl. No.: 12/094,945

(22) PCT Filed: Nov. 16, 2006

(86) PCT No.: PCT/EP2006/010979
§ 371 (c)(1),
(2), (4) Date: May 23, 2008

(87) PCT Pub. No.: WO2007/062748
PCT Pub. Date: Jun. 7, 2007

(65) Prior Publication Data
US 2008/0305953 A1 Dec. 11, 2008

(30) Foreign Application Priority Data
Nov. 29, 2005 (DE) .......................... 10 2005 056 744

(51) Int. Cl.
*A01N 25/32* (2006.01)
*A01N 43/00* (2006.01)
(52) U.S. Cl. .................. 504/139; 504/106; 504/280
(58) Field of Classification Search .................. 504/139, 504/106
See application file for complete search history.

(56) References Cited

U.S. PATENT DOCUMENTS

| 5,491,125 A | 2/1996 | Albrecht et al. |
| 6,455,471 B1 | 9/2002 | Gubelmann-Bonneau et al. |
| 2002/0016263 A1 | 2/2002 | Wurtz et al. |
| 2004/0132621 A1* | 7/2004 | Frisch et al. ................... 504/363 |
| 2005/0026786 A1 | 2/2005 | Deckwer et al. |
| 2005/0032647 A1 | 2/2005 | Deckwer et al. |
| 2005/0233906 A1 | 10/2005 | Schnabel et al. |

FOREIGN PATENT DOCUMENTS

| WO | WO 96/26206 | 8/1996 |
| WO | WO 96/37101 | 11/1996 |
| WO | WO 00/21924 | 4/2000 |
| WO | WO 01/74785 A1 | 10/2001 |
| WO | WO 2004/080178 A1 | 9/2004 |
| WO | WO 2005/055714 A2 | 6/2005 |
| WO | WO 2005/089548 A1 | 9/2005 |

* cited by examiner

*Primary Examiner* — Rebecca Prouty
*Assistant Examiner* — Danielle Sullivan
(74) *Attorney, Agent, or Firm* — Baker Donelson Bearman, Caldwell & Berkowitz PC

(57) ABSTRACT

Liquid formulations containing herbicidal actives from the group of HPPD inhibitors, dialkyl sulfosuccinates, surfactants and solvents are provided. The present invention relates to liquid formulations comprising: A) one or more HPPD inhibitors, B) one or more dialkyl sulfosuccinates, C) one or more further surfactants, D) one or more solvents, E) further auxiliaries and additives, and F) one or more non-A) agrochemical actives. The liquid formulations are suitable for use in the field of crop protection.

18 Claims, No Drawings

LIQUID FORMULATIONS CONTAINING DIALKYL SULFOSUCCINATE AND HYDROXYPHENYLPYRUVATE DIOXYGENASE INHIBITORS

The present invention pertains to the field of crop protection formulations. More particularly the invention pertains to liquid formulations comprising dialkyl sulfosuccinates and herbicidal actives that are known as inhibitors of hydroxyphenylpyruvate dioxygenase (HPPD).

Herbicidal actives are typically not used in their pure form. Depending on the field of application and the mode of application, and also on physical, chemical, and biological parameters, the actives are used in a mixture with typical auxiliaries and additives, as an active compound formulation. Also known are the combinations with further actives for the purpose of extending the spectrum of activity and/or for protecting the crop plants (e.g., by safeners, antidotes).

Formulations of herbicidal actives ought generally to have a high chemical and physical stability, good application properties and user friendliness, and a broad biological activity with high selectivity.

From the series of the inhibitors of hydroxyphenylpyruvate dioxygenase, isoxaflutole, sulcotrione, and mesotrione have been available commercially for some time. As formulations of these actives, suspension concentrates and water-dispersible granules are already known: see, for example, "The Pesticide Manual" 13th edition (2003), The British Crop Protection Council.

On the part of users, depending on the purpose of application, there is also demand for liquid formulations in which the components are in complete or near-complete solution. Such formulations, however, cannot easily be prepared from all actives: often, deficient solubility in solvents and/or deficient chemical stability of the active makes its formulation in liquid form an unlikely possibility.

It was an object of the present invention to provide liquid formulations for actives from the series of the HPPD inhibitors that do not exhibit the disadvantages stated above.

This object is achieved by means of liquid formulations which as well as HPPD inhibitors also comprise dialkyl sulfosuccinates, further surfactants, and certain solvents.

The present invention accordingly provides liquid formulations comprising

A) one or more herbicidal actives from the group of HPPD inhibitors,
B) one or more surfactants from the group of dialkyl sulfosuccinates,
C) one or more other non-B) surfactants, and
D) one or more solvents, the molar ratio of HPPD inhibitor to dialkyl sulfosuccinate being less than or equal to 1:6.

The liquid formulations of the invention exhibit outstanding storage stability and do not tend to form undissolved constituents.

The liquid formulations of the invention may where appropriate, besides components A) to D), include auxiliaries and additives as further components, examples being the following:

E) typical formulation assistants such as defoamers, evaporation retardants, odorants, colorants, frost preventatives or preservatives, and
F) one or more further non-A) agrochemical actives such as herbicides, insecticides, fungicides, safeners, growth regulators or fertilizers.

Examples of suitable liquid formulations include emulsifiable concentrates (EC), microemulsions, microemulsion concentrates, concentrated emulsions (EW) such as oil-in-water and water-in-oil emulsions, sprayable solutions or emulsions, suspoemulsions, oil-based dispersions (OD) and oil-miscible solutions (OL). Emulsifiable concentrates are preferred. These types of formulation are known in principle and are described for example in: Winnacker-Küchler, "Chemische Technologie", volume 7, C. Hauser Verlag, Munich, 4th ed. 1986, Wade van Valkenburg, "Pesticide Formulations", Marcel Dekker, N.Y., 1973; K. Martens, "Spray Drying" Handbook, 3rd ed. 1979, G. Goodwin Ltd. London.

The HPPD inhibitors possess an acidic proton which can be removed by a base. The HPPD inhibitor salts that are obtainable accordingly are likewise suitable as component A, in the liquid formulations of the invention. Examples of suitable bases include ammonia, the hydroxides, carbonates, and hydrogen carbonates of zinc, alkali metals and alkaline earth metals, such as sodium, potassium, calcium, and magnesium, and organic bases of the formula $NR^1R^2R^3$ in which $R^1$, $R^2$, and $R^3$ may in each case be $(C_1-C_{20})$-alkyl, $(C_2-C_{20})$-alkenyl or $(C_3-C_{20})$-alkynyl, and $R^2$ and $R^3$ may, furthermore, also be hydrogen. Preference is given to the potassium, sodium, and ammonium salts.

In one preferred embodiment these liquid formulations comprise HPPD inhibitors of the formula (I),

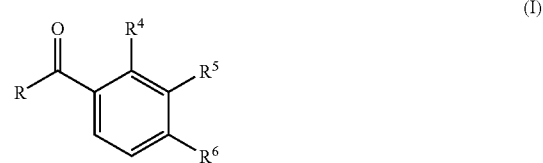

(I)

in which

R is cyclohexane-1,3-dion-2-yl, 5-hydroxy-1H-pyrazol-4-yl or isoxazol-4-yl, these three rings being unsubstituted or being substituted by one or two radicals from the group consisting of methyl, ethyl, propyl, and cyclopropyl;

$R^4$ is methyl, methoxy, trifluoromethoxy, trifluoromethyl, methylsulfonyl, chloro or bromo;

$R^5$ is hydrogen, methyl, methoxy, trifluoromethoxy, trifluoromethyl, chloro, bromo, 2,2,2-trifluoroethoxymethyl or 4,5-dihydroisoxazol-3-yl;

$R^6$ is chloro, bromo, trifluoromethoxy, trifluoromethyl or methylsulfonyl.

In one particularly preferred embodiment, these liquid formulations comprise HPPD inhibitors A-1 to A-6:

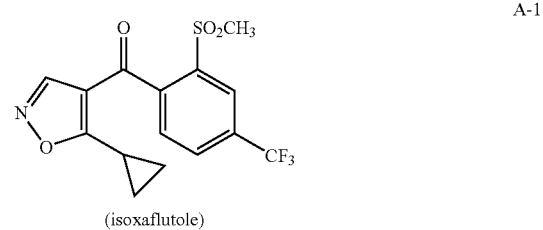

(isoxaflutole)

A-1

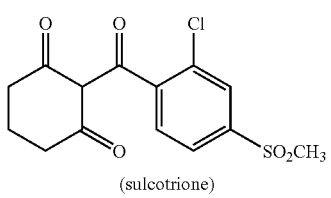

(sulcotrione) A-2

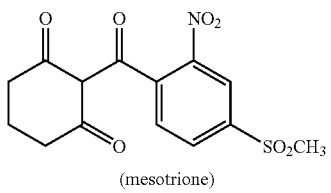

(mesotrione) A-3

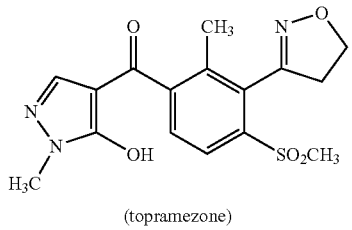

(topramezone) A-4

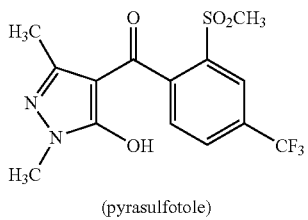

(pyrasulfotole) A-5

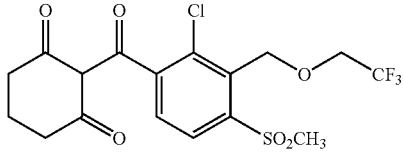

A-6

The HPPD inhibitors present as component A) are known, for example, from WO 1996/26206, WO 00/21924, WO 01/74785, from "The Pesticide Manual" 13th edition (2003), The British Crop Protection Council, and from the Web page http://www.hclrss.demon.co.uk, and in some cases are already available commercially.

In one preferred embodiment the liquid formulations of the invention comprise
A) 0.1% to 50% of one or more HPPD inhibitors,
B) 1% to 50% of one or more dialkyl sulfosuccinates,
C) 2% to 40% of one or more further surfactants,
D) 5% to 80% of one or more solvents,
E) 0% to 25% of further auxiliaries and additives, and
F) 0% to 50% of one or more further non-A) agrochemical actives.

In one particularly preferred embodiment these liquid formulations comprise
A) 0.5% to 25% of one or more HPPD inhibitors,
B) 2% to 25% of one or more dialkyl sulfosuccinates,
C) 5% to 25% of one or more further surfactants,
D) 10% to 80% of one or more solvents,
E) 0% to 20% of further auxiliaries and additives, and
F) 0% to 40% of one or more further non-A) agrochemical actives.

All % figures are percentages by weight.

Suitable dialkyl sulfosuccinates B) are those of the general formula (II):

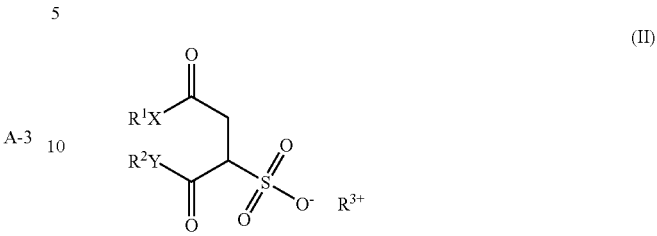

in which
$R^1$, $R^2$ independently of one another and identically or differently are hydrogen, an unsubstituted or substituted $C_1$-$C_{30}$ hydrocarbon radical such as $C_1$-$C_{30}$ alkyl, or a (poly)alkylene oxide adduct,
$R^{3+}$ is a cation, e.g., a metal cation such as an alkali metal or alkaline earth metal cation, an ammonium cation such as $^+NH_4$, alkyl-, alkylaryl- or poly(arylalkyl)phenyl-ammonium cation or its (poly)alkylene oxide adducts, or an amino-terminated (poly)alkylene oxide adduct, and
X, Y independently of one another and identically or differently are O or $^+NR^4$,
in which $R^4$ is hydrogen, an unsubstituted or substituted $C_1$-$C_{30}$ hydrocarbon radical such as $C_1$-$C_{30}$ alkyl, $C_1$-$C_{30}$ alkyl-$C_6$-$C_{14}$ aryl or poly($C_6$-$C_{14}$-aryl-$C_1$-$C_{30}$-alkyl)phenyl, dicarboxyethyl or a (poly)alkylene oxide adduct.

Examples of commercially available sulfosuccinates B) which are preferred in the context of the present invention are set out hereinbelow: sodium dialkyl sulfosuccinates, e.g. Na diisooctyl sulfosuccinate, available commercially in the form, for example, of Aerosol® products (Cytec), Agrilan® or Lankropol® products (Akzo Nobel), Empimin® products (Albright&Wilson), Cropol® products (Croda), Lutensit® products (BASF) or Imbirol®, Madeol® or Polirol® products (Cesalpinia), or sodium di(2-ethylhexyl) sulfosuccinates, available commercially in the form, for example, of Triton® products (Union Carbide) such as Triton® GR-5M and Triton® GR-7ME, disodium alcohol polyethylene glycol ether semisulfosuccinate, available commercially in the form, for example, of Aerosol® products (Cytec), of Marlinat® or Sermul® products (Condea), of Empicol® products (Albright&Wilson), of Secosol® products (Stepan), of Geropon® products (Rhodia), of Disponil® or Texapon® products (Cognis) or of Rolpon® products (Cesalpinia), disodium N-alkylsulfosuccinamate, available commercially in the form, for example, of Aerosol® products (Cytec), of Rewopol® or Rewoderm® products (Rewo), of Empimin® products (Albright&Wilson), of Geropon® products (Rhodia) or of Polirol® products (Cesalpinia), disodium fatty acid amide polyethylene glycol ether sulfosuccinate, available commercially in the form, for example, of Elfanol® or Lankropol® products (Akzo Nobel), of Rewoderm®, Rewocid® or Rewopol® products (Rewo), of Emcol® products (Witco), of Standapol® products (Cognis) or of Rolpon® products (Cesalpinia), and tetrasodium N-(1,2-dicarboxyethyl)-N-octadecyl-sulfosuccinamate, available commercially in the form, for example, of Aerosol 22® (Cytec).

Examples of suitable surfactants C) are surfactants on a nonaromatic basis, based for example on heterocycles, olefins, aliphatics or cycloaliphatics, examples being surface-active compounds substituted by one or more alkyl groups and subsequently derivatized, e.g., alkoxylated, sulfated, sulfonated or phosphated pyridine, pyrimidine, trazine, pyrrol, pyrrolidine, furan, thiophene, benzoxazole, benzothiazole, and triazole compounds, and/or surfactants on an aromatic basis, e.g., phenois or benzenes substituted by one or more alkyl groups and subsequently derivatized, e.g., alkoxylated, sulfated, sulfonated or phosphatized. The surfactants C) are generally soluble in the solvent phase and suitable for emulsifying that phase—together with actives dissolve therein—on dilution with water (to give a spray liquor). The formulations of the invention may comprise, for example, nonaromatic or aromatic surfactants or mixtures of nonaromatic and aromatic surfactants.

Examples of surfactants C) are listed below, where EO=ethylene oxide units, PO=propylene oxide units, and BO=butylene oxide units:

C1) $C_{10}$-$C_{24}$ alcohols, which may be alkoxylated, with for example 1-60 alkylene oxide units, preferably 1-60 EO and/or 1-30 PO and/or 1-15 BO in any order. The terminal hydroxyl groups of these compounds may be end-group-capped by an alkyl, cycloalkyl or acyl radical having 1-24 carbon atoms. Examples of such compounds are:
Genapol® C, L, O, T, UD, UDD, X products from Clariant, Plurafac® and Lutensol® A, AT, ON, TO products from BASF, Marlipal® 24 and O13 products from Condea, Dehypon® products from Henkel, and Ethylan® products from Akzo-Nobel such as Ethylan CD 120.

C2) anionic derivatives of the products described under C1), in the form of ether carboxylates, sulfonates, sulfates, and phosphates, and their inorganic (e.g., alkali metal and alkaline earth metal) and organic salts (e.g., based on amine or alkanol amine), such as Genapol® LRO, Sandopan® products, and Hostaphat/Hordaphos® products from Clariant. Copolymers composed of EO, PO and/or BO units such as, for example, block copolymers such as the Pluronic® products from BASF and the Synperonic® products from Uniqema having a molecular weight of 400 to 108. Alkylene oxide adducts of $C_1$-$C_9$ alcohols such as Atlox® 5000 from Uniqema or Hoe®-S3510 from Clariant.

C3) fatty acid alkoxylates and triglyceride alkoxylates such as the Serdox® NOG products from Condea or alkoxylated vegetable oils such as soybean oil, rapeseed oil, corn germ oil, sunflower oil, cottonseed oil, linseed oil, coconut oil, palm oil, thistle oil, walnut oil, peanut oil, olive oil or castor oil, especially rapeseed oil, the vegetable oils also comprehending their transesterification products, examples being alkyl esters such as rapeseed oil methyl ester or rapeseed oil ethyl ester, examples being the Emulsogen® products from Clariant, salts of aliphatic, cycloaliphatic, and olefinic carboxylic acids and polycarboxylic acids, and also alpha-sulfo fatty acid esters of the kind obtainable from Henkel.

C4) fatty acid amide alkoxylates such as the Comperlan® products from Henkel or the Amam® products from Rhodia. Alkylene oxide adducts of alkynediols such as the Surfynol® products from Air Products. Sugar derivatives such as amino sugars and amido sugars from Clariant, glucitols from Clariant, alkylpolyglycosides in the form of the APG® products from Henkel or such as sorbitan esters in the form of the Span® or Tween® products from Uniqema or cyclodextrin esters or ethers from Wacker.

C5) surface-active cellulose derivatives and algin derivatives, pectin derivatives, and guar derivatives such as the Tylose® products from Clariant, the Manutex® products from Kelco, and guar derivatives from Cesalpina. Alkylene oxide adducts based on polyols, such as Polyglykol® products from Clariant. Surface-active polyglycerides and derivatives thereof from Clariant.

C6) alkanesulfonates, paraffinsulfonates, and olefinsulfonates such as Netzer IS®, Hoe® S1728, Hostapur® OS, Hostapur® SAS from Clariant, C7) alkylene oxide adducts of fatty amines, quaternary ammonium compounds with 8 to 22 carbon atoms ($C_8$-$C_{22}$) such as, for example, the Genamin®C, L, O, and T products from Clariant.

C8) surface-active zwitterionic compounds such as taurides, betaines, and sulfobetaines in the form of Tegotain® products from Goldschmidt, Hostapon® and Arkopon® products from Clariant.

C9) surface-active compounds based on silicone or silane such as the Tegopren® products from Goldschmidt and the SE® products from Wacker, and also the Bevaloid®, Rhodorsil®, and Silcolapse® products from Rhodia (Dow Corning, Reliance, GE, Bayer).

C10) perfluorinated or polyfluorinated surface-active compounds such as Fluowet® products from Clariant, the Bayowet® products from Bayer, the Zonyl® products from DuPont, and products of this kind from Daikin and Asahi Glass.

C11) surface-active sulfonamides such as those from Bayer.

C12) surface-active polyacrylic and polymethacrylic derivatives such as the Sokalan® products from BASF.

C13) surface-active polyamides such as modified gelatins or derivatized polyaspartic acid from Bayer, and derivatives thereof.

C14) polyvinyl-type surfactant compounds such as modified polyvinylpyrrolidone such as the Luviskol® products from BASF and the Agrimer® products from ISP or the derivatized polyvinyl acetates such as the Mowilith® products from Clariant or the corresponding butyrates such as the Lutonal® products from BASF, the Vinnapas® and the Pioloform® products from Wacker, or modified polyvinyl alcohols such as the Mowiol® products from Clariant.

C15) surface-active polymers based on maleic anhydride and/or reaction products of maleic anhydride, and also copolymers containing maleic anhydride and/or reaction products of maleic anhydride, such as the Agrimer® VEMA products from ISP.

C16) surface-active derivatives of montan waxes, polyethylene waxes, and polypropylene waxes, such as the Hoechst® waxes or the Licowet® products from Clariant.

C17) surface-active phosphonates and phosphinates such as Fluowet® PL from Clariant.

C18) polyhalogenated or perhalogenated surfactants such as, for example, Emulsogen® 1557 from Clariant.

C19) phenols, which may have been alkoxylated, examples being phenyl ($C_1$-$C_4$)alkyl ethers or (poly)alkoxylated phenols [i.e., phenol-(poly)alkylene glycol ethers], having for example 1 to 50 alkyleneoxy units in the (poly)alkyleneoxy moiety, the alkylene moiety having preferably in each case 1 to 4 carbon atoms, preferably phenol reacted with 3 to 10 mol of alkylene oxide, (poly)alkylphenols or (poly)alkylphenol alkoxylates [i.e., polyalkylphenol-(poly)alkylene glycol ethers], having for example 1 to 12 carbon atoms per alkyl radical and 1 to 150 alkyleneoxy units in the polyalkyleneoxy moiety, preferably triisobutylphenol or tri-n-butylphenol reacted with 1 to 50 mol of ethylene oxide, polyarylphenols or polyarylphenol alkoxylates [i.e., polyarylphenol-(poly)alkylene glycol ethers], for example, tristyrylphenol polyalkylene glycol ethers having 1 to 150 alkyleneoxy units in the polyalkyleneoxy moiety, preferably tristyrylphenol reacted with 1 to 50 mol of ethylene oxide.

C20) compounds which formally constitute the reaction products of the molecules described under C19) with sulfuric acid or phosphoric acid and salts thereof neutralized with suitable bases, examples being the acidic phosphoric ester of triply ethoxylated phenol, the acidic phosphoric ester of a nonylphenol reacted with 9 mol of ethylene oxide, and the triethanolamine-neutralized phosphoric ester of the reaction product of 20 mol of ethylene oxide and 1 mol of tristyrylphenol.

C21) benzenesulfonates such as alkyl- or arylbenzenesulfonates, examples being acidic (poly)alkyl- and (poly)aryl-benzenesulfonates and (poly)alkyl- and (poly)aryl-benzenesulfonates neutralized with appropriate bases, having for example 1 to 12 carbon atoms per alkyl radical and/or having up to 3 styrene units in the polyaryl radical, preferably (linear) dodecylbenzenesulfonates and their oil-soluble salts such as, for example, the calcium salt or the isopropylammonium salt of dodecylbenzenesulfonic acid.

Preferred among the alkyleneoxy units are ethyleneoxy, propyleneoxy, butyleneoxy units, especially ethyleneoxy units.

Examples of surfactants from the group of nonaromatic-based surfactants are the surfactants of aforementioned groups C1) to C18), preferably those of groups C1), C2), C6), and C7). Examples of surfactants from the group of surfactants on an aromatic basis are the surfactants of above-mentioned groups C19) to C21), preferably phenol reacted with 4 to 10 mol of ethylene oxide, available commercially in the form, for example, of the Agrisol® products (Akcros), tri-isobutylphenol reacted with 4 to 50 mol of ethylene oxide, available commercially in the form, for example, of the Sapogenat® T products (Clariant), nonylphenol reacted with 4 to 50 mol of ethylene oxide, available commercially in the form, for example, of the Arkopal® products (Clariant), tristyrylphenol reacted with 4 to 150 mol of ethylene oxide, as, for example, from the Soprophor® series such as Soprophor® FL, Soprophor® 3D33, Soprophor® BSU, Soprophor® 4D-384, Soprophor® CY/8 (Rhodia), and acidic (linear) dodecylbenzenesulfonate, available commercially in the form, for example, of the Marlon® products (Hüls).

Preferred surfactants C) are, for example, alkoxylated $C_{10}$-$C_{24}$ alcohols (C1) and their anionic derivatives (C2) such as sulfates, sulfonates, and phosphates, alkoxylated vegetable oils (C3), akoxylated phenols (C19) and their reaction products with sulfuric acid or phosphoric acid (C20), and alkylbenzenesulfonates (C21).

Examples of suitable solvents D) are nonpolar, polar protic or aprotic dipolar solvents, and mixtures thereof. Examples of such solvents are aliphatic or aromatic hydrocarbons, such as mineral oils, paraffins or toluene, xylenes and naphthalene derivatives, more particularly 1-methylnaphthalene, 2-methylnaphthalene, $C_6$-$C_{16}$ aromatics mixtures such as, for example, the Solvesso® series (ESSO) with the products Solvesso® 100 (p.p. 162-177° C.), Solvesso® 150 (p.p. 187-207° C.), and Solvesso® 200 (p.p. 219-282° C.), and 6-20 C aliphatics, which may be linear or cyclic, such as the products of the Shellsol® series, grades T and K or BP-n paraffins, halogenated aliphatic or aromatic hydrocarbons such as methylene chloride and chlorobenzene, mono basic and/or polybasic esters such as triacetin (acetic triglyceride), butyrolactone, propylene carbonate, triethyl citrate, and ($C_1$-$C_{22}$)alkyl phthalates, especially ($C_4$-$C_8$)alkyl phthalates, for example, ethers such as diethyl ether, tetrahydrofuran (THF), dioxane, alkylene glycol monoalkyl ethers and dialkyl ethers such as, for example, propylene glycol monomethyl ether, especially Dowanol® PM (propylene glycol monomethyl ether), propylene glycol monoethyl ether, ethylene glycol monomethyl ether or monoethyl ether, diglyme and tetraglyme, ketones, examples being water-miscible ketones such as acetone, or water-immiscible ketones such as cyclohexanone or isophorone, nitriles such as acetonitrile, propionitrile, butyronitrile, and benzonitrile, sulfoxides and sulfones such as dimethyl sulfoxide (DMSO) and sulfolane, and also oils of natural origin, examples being vegetable oils such as corn germ oil and rapeseed oil and their transesterification products such as rapeseed oil methyl ester, and water.

Preferred further organic solvents are, more particularly, aromatic solvents such as the Solvesso® series from Exxon, acetophenone, and water-miscible ketones such as acetone.

The liquid formulations may also comprise further agrochemical actives E) such as herbicides, fungicides, insecticides, safeners, and fertilizers such as ammonium sulfate, ammonium hydrogen sulfate, urea or mixtures thereof, and/or growth regulators. These actives are known to the skilled worker from, for example, "The Pesticide Manual", 13th edition (2003), The British Crop Protection Council.

Suitable non-component-A) agrochemical actives which may be present optionally as component E) in the liquid formulations of the invention are preferably herbicidal actives, for example:

EA) herbicides of the type of the phenoxyphenoxy- and heteroaryloxyphenoxycarboxylic acid derivatives, such as EA1) phenoxyphenoxy- and benzyloxyphenoxycarboxylic acid derivatives, for example methyl 2-(4-(2,4-dichlorophen-oxy)phenoxy)propionate (diclofop-methyl), methyl 2-(4-(4-bromo-2-chlorophenoxy)phenoxy)propionate (DE-A-2601548), methyl 2-(4-(4-bromo-2-fluorophenoxy)phenoxy)propionate (U.S. Pat. No. 4,808,750), methyl 2-(4-(2-chloro-4-trifluoromethylphenoxy)phenoxy)propionate (DE-A-2433067), methyl 2-(4-(2-fluoro-4-trifluoromethylphenoxy)phenoxy)propionate (U.S. Pat. No. 4,808,750), methyl 2-(4-(2,4-dichlorobenzyl)phenoxy)propionate (DE-A-2417487), ethyl 4-(4-(4-trifluoromethylphenoxy)phenoxy)pent-2-enoate, methyl 2-(4-(4-trifluoromethylphenoxy)phenoxy)propionate (DE-A-2433067);

EA2) "monocyclic" heteroaryloxyphenoxyalkanecarboxylic acid derivatives, for example ethyl 2-(4-(3,5-dichloropyridyl-2-oxy)phenoxy)propionate (E P-A-0002925), propargyl 2-(4-(3,5-dichloropyridyl-2-oxy)phenoxy)propionate (EP-A-0003114), methyl 2-(4-(3-chloro-5-trifluoromethyl-2-pyridyloxy)phenoxy)propionate (EP-A-0003890), ethyl 2-(4-(3-chloro-5-trifluoromethyl-2-pyridyloxy)phenoxy)propionate (EP-A-0003890), propargyl 2-(4-(5-chloro-3-fluoro-2-pyridyloxy)phenoxy)propionate (EP-A-0191736), butyl 2-(4-(5-trifluoromethyl-2-pyridyloxy)phenoxy)propionate (fluazifop-butyl);

EA3) "bicyclic" heteroaryloxyphenoxyalkanecarboxylic acid derivatives, for example methyl and ethyl 2-(4-(6-chloro-2-quinoxalyloxy)phenoxy)propionate (quizalofopmethyl and quizalofopethyl), methyl 2-(4-(6-fluoro-2-quinoxalyloxy)phenoxy)propionate (see J. Pest. Sci. Vol. 10, 61 (1985)), 2-isopropylideneaminooxyethyl 2-(4-(6-chloro-2-quinoxalyloxy)phen-oxy)propionate (propaquizafop), ethyl 2-(4-(6-chlorobenzoxazol-2-yloxy)phenoxy)propionate (fenoxaprop-ethyl), its D(+) isomer (fenoxaprop-P-ethyl EX) and ethyl 2-(4-(6-chlorobenzothiazol-2-yloxy)phenoxy)propionate (DE-A-2640730), tetrahydro-2-furylmethyl 2-(4-(6-chloroquinoxalyloxy)phenoxy)propionate (EP-A-0323727);

EB) chloroacetanilides, for example

N-methoxymethyl-2,6-diethyl-chloroacetanilide (alachlor),

N-(3-methoxyprop-2-yl)-2-methyl-6-ethylchloroacetanilide (metolachlor), 2,6-dimethyl-N-(3-methyl-1,2,4-oxadiazol-5-ylmethyl)chloroacetanilide, N-(2,6-dimethylphenyl)-N-(1-pyrazolylmethyl)chloroacetamide (metazachlor);

EC) thiocarbamates, for example

S-ethyl N,N-dipropylthiocarbamate (EPTC),

S-ethyl N,N-diisobutylthiocarbamate (butylate);

ED) cyclohexanedione oximes, for example methyl 3-(1-allyloxyiminobutyl)-4-hydroxy-6,6-dimethyl-2-oxocyclohex-3-enecarboxylate (alloxydim), 2-(1-ethoxyiminobutyl)-5-(2-ethylthiopropyl)-3-hydroxycyclohex-2-ene-1-one (sethoxydim), 2-(1-ethoxyiminobutyl)-5-(2-phenylthiopropyl)-3-hydroxycyclohex-2-ene-1-one (cloproxydim), 2-(1-(3-chloroallyloxy)iminobutyl)-5-(2-ethylthiopropyl)-3-hydroxycyclohex-2-ene-1-one, 2-(1-(3-chloroallyloxy)iminopropyl)-5-(2-ethylthiopropyl)-3-hydroxycyclohex-2-ene-1-one (clethodim), 2-(1-ethoxyiminobutyl)-3-hydroxy-5-(thian-3-yl)cyclohex-2-enone (cycloxydim), 2-(1-ethoxyiminopropyl)-5-(2,4,6-trimethylphenyl)-3-hydroxycyclohex-2-ene-1-one (tralkoxydim);

EE) benzoylcyclohexanediones, for example 2-(2-chloro-4-methylsulfonylbenzoyl)cyclohexane-1,3-dione (SC-0051, EP-A-0137963), 2-(2-nitrobenzoyl)-4,4-dimethylcyclohexane-1,3-dione (EP-A-0274634), 2-(2-nitro-4-methylsulfonylbenzoyl)-4,4-dimethyl-cyclohexane-1,3-dione (WO 91/13548 mesotrione);

EF) S—(N-aryl-N-alkylcarbamoylmethyl) dithiophosphonates, such as S—[N-(4-chlorophenyl)-N-isopropylcarbamoyl methyl] O,O-dimethyl dithio-phosphate (anilophos);

EG) alkylazines, such as, for example, described in WO-A-97/08156, WO-A-97/31904, DE-A-19826670, WO-A-98/15536, WO-A-98/15537, WO-A-98/15538, WO-A-98/15539 and also DE-A-19828519, WO-A-98/34925, WO-A-98/42684, WO-A-99/18100, WO-A-99/19309, WO-A-99/37627 and WO-A-99/65882, preferably those of the formula (G)

(G)

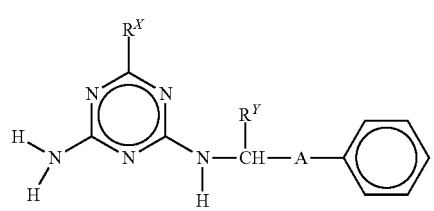

in which $R^X$ is $(C_1-C_4)$-alkyl or $(C_1-C_4)$-haloalkyl;

$R^Y$ is $(C_1-C_4)$-alkyl, $(C_3-C_6)$-cycloalkyl or $(C_3-C_6)$-cycloalkyl-$(C_1-C_4)$-alkyl and A is —CH$_2$—, —CH$_2$—CH$_2$—, —CH$_2$—CH$_2$—CH$_2$—, —O—, —CH$_2$—CH$_2$—O—, —CH$_2$—CH$_2$—CH$_2$—O—, more preferably those of the formulae G1-G7

(G1)

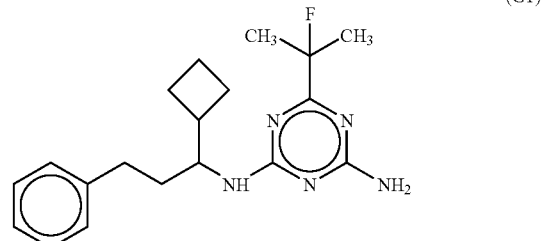

(G2)

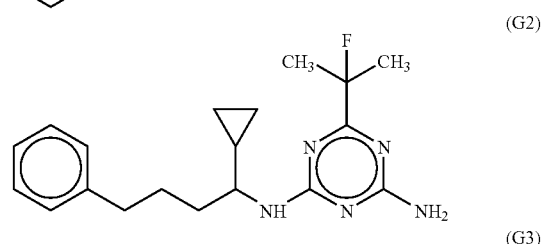

(G3)

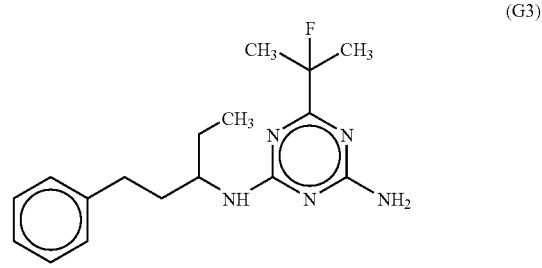

(G4)

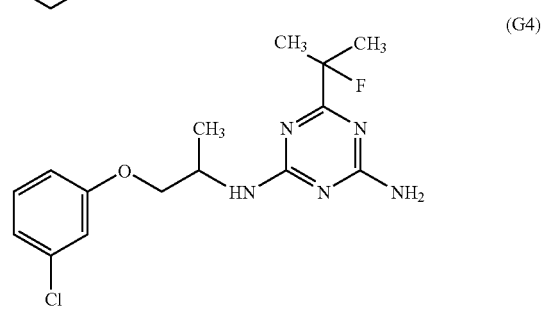

(G5)

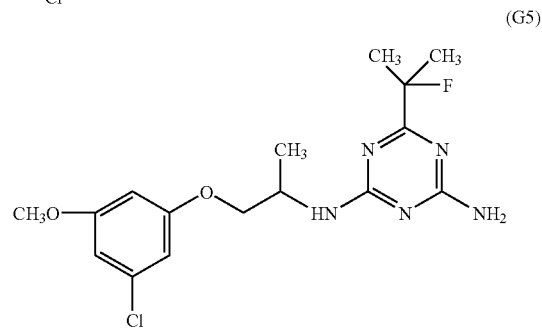

more particularly, the known actives listed below, as described, for example, in Weed Research 26, 441-445 (1986), or in "The Pesticide Manual", 13th edition, The British Crop Protection Council 2003, and the literature cited therein, for example in formulated mixtures or as components for tank mixes. The compounds are referred to either by the common name according to the International Organization for Standardization (ISO) or by the chemical name, if appropriate together with a customary code number, and include in each case all use forms, such as acids, salts, esters and isomers, such as stereoisomers and optical isomers: acetochlor; acifluorfen; aclonifen; AKH 7088, i.e. [[[1-[5-[2-chloro-4-(trifluoromethyl)phenoxy]-2-nitrophenyl]-2-methoxyethylidene]amino]-oxy]acetic acid and methyl [[[1-[5-[2-chloro-4-(trifluoromethyl)phenoxy]-2-nitrophenyl]-2-methoxyethylidene]amino]oxy]acetate; alachlor; alloxydim; ametryn; amitrol; AMS, i.e. ammonium sulfamate; anilofos; asulam; atrazine; azafenidine (DPX-R6447); aziprotryn; barban; BAS 516H, i.e. 5-fluoro-2-phenyl-4H-3,1-benzoxazin-4-one; benazolin; benfluralin; benfuresate; bensulide; bentazone; benzofluor; benzoylprop-ethyl; benzthiazuron; bialaphos; bifenox; bispyribac-sodium (KIH-2023), bromacil; bromobutide; bromofenoxim; bromoxynil, in particular bromoxynil-octanoate and bromoxynil-heptanoate; butachlor; butamifos; butenachlor; buthidazole; butralin; butroxydim (ICI-0500), butylate; cafenstrole (CH-900); carbetamide; cafentrazone; CDAA, i.e. 2-chloro-N,N-di-2-propenyl-acetamide; CDEC, i.e. 2-chloroallyl diethyldithiocarbamate; chlomethoxyfen; chloramben; cloransulam-methyl (XDE-565), chlorazifop-butyl, chlorbromuron; chlorbufam; chlorfenac; chlorflurenol-methyl; chloridazon; chlornitrofen; chlorotoluron; chloroxuron; chlorpropham; chlorthal-dimethyl; chlorthiamid; cinidon-ethyl, cinmethylin; clethodim; clodinafop and its ester derivatives (for example clodinafop-propargyl); clomazone; clomeprop; cloproxydim; clopyralid; cumyluron (JC 940); cyanazine; cycloate; cycloxydim; cycluron; cyhalofop and its ester derivatives (for example the butyl ester, DEH-112); cyperquat; cyprazine; cyprazole; 2,4-D; 2,4-DB; dalapon; desmedipham; desmetryn; di-allate; dicamba; dichlobenil; dichlorprop; diclofop and its esters, such as diclofop-methyl; diclosulam (XDE-564), diethatyl; difenoxuron; difenzoquat; diflufenican; diflufenzopyr-sodium (SAN-835H), dimefuron; dimethachlor; dimethametryn; dimethenamid (SAN-582H); dimidazone, methyl 5-(4,6-dimethylpyrimidin-2-ylcarbamoylsulfamoyl)-1-(2-pyridyl)pyrazole-4-carboxylate (NC-330); triaziflam (IDH-1105), cinosulfon; dimethipin, dinitramine; dinoseb; dinoterb; diphenamid; dipropetryn; diquat; dithiopyr; diuron; DNOC; eglinazine-ethyl; EL 177, i.e. 5-cyano-1-(1,1-dimethylethyl)-N-methyl-1H-pyrazole-4-carboxamide; endothal; indanofan (MK-243), EPTC; esprocarb; ethalfluralin; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]phenyl]ethanesulfonamide; ethoxyfen and its esters (for example the ethyl ester, HN-252); etobenzanid (HW 52); 3-(4-ethoxy-6-ethyl-1,3,5-triazin-2-yl)-1-(2,3-dihydro-1,1-dioxo-2-methylbenzo[b]thiophene-7-sulfonyl) urea (EP-A 079 683); 3-(4-ethyl-6-methoxy-1,3,5-triazin-2-yl)-1-(2,3-dihydro-1,1-dioxo-2-methyl-benzo[b]thiophene-7-sulfonyl)urea (EP-A-079683); fenoprop; clomazone, fenoxapropand fenoxaprop-P and their esters, for example fenoxaprop-P-ethyl and fenoxaprop-ethyl; butroxydimfenuron; flamprop-methyl; flufenacet (BAY-FOE-5043), fluazifop and fluazifop-P and their esters, for example fluazifop-butyl and fluazifop-P-butyl, florasulam (DE-570); fluchloralin; flumetsulam; fluometuron; flumiclorac and its esters (for example the pentyl ester, S-23031); flumioxazin (S-482); flumipropyn (KNW-739); fluorodifen; fluoroglycofen-ethyl; fluropacil (UBIC-4243); fluridone; fluorochloridone; fluoroxypyr; flurtamone; fluthiacet-methyl (KIH-9201), fomesafen; fosamine; furyloxyfen; glufosinate; glyphosate; halosafen; halosulfuron and its esters (for example methyl ester, NC-319); haloxyfop and its esters; haloxyfop-P (=R-haloxyfop) and its esters; hexazinone; imazamethabenz-methyl; imazamox (AC-299263), imazapyr; imazaquin and salts thereof, such as the ammonium salt; imazapic; imazethapyr; imazosulfuron; ioxynil; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; methabenzthiazuron; metam; methazole; methoxyphenone; methyldymron; metobenzuron, mesosulfuron-methyl, mesosulfuron-methyl (WO 95/10507); metobromuron; metolachlor; S-metolachlor, metosulam (XRD 511); metoxuron; metribuzin; maleic hydrazide; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; foramsulfuron (WO 95/01344); naproanilide; napropamide; naptalam; NC 310, i.e. 4-(2,4-dichlorobenzoyl)-1-methyl-5-benzyloxypyrazole; neburon; nipyraclophen; nitralin; nitrofen; nitrofluorfen; norflurazon; orbencarb; oryzalin; oxadiargyl (RP-020630); oxadiazon; oxaziclomefone (MY-100), oxyfluorfen; paraquat; pebulate; pendimethalin; pentoxazone (KPP-314), perfluidone; phenisopham; phenmedipham; picloram; pinoxaden; piperophos; pyributicarb; pirifenop-butyl; pretilachlor; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prynachlor; pyraflufen-ethyl (ET-751), chloridazon; pyrazoxyfen; pyribenzoxim, pyridate; pyriminobac-methyl (KIH-6127), pyrithiobac (KIH-2031); pyroxofop and its esters (for example propargyl ester); quinclorac; quinmerac; quizalofop, quizalofop and quizalofop-P and their ester derivatives, for example quizalofop-ethyl; quizalofop-P-tefuryl and -ethyl; S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl) phenoxy]-2-naphthalenyl]oxy]propanoic acid and methyl 2-[[7-[2-chloro-4-(trifluoromethyl)phenoxy]-2-naphthalenyl]oxy]propanoate; flazasulfuron (FMC-97285, F-6285); sulfazuron; glyphosate-trimesium (ICI-A0224); TCA; tebutam (GCP-5544); tebuthiuron; tepraloxydim (BAS-620H), terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiazafluoron; thiazopyr (Mon-13200); thidiazimin (SN-124085); thiobencarb; tiocarbazil; tralkoxydim; tri-allate; triazofenamide; triclopyr; tridiphane; trietazine; trifluralin; trimeturon; vernolate; WL 110547, i.e. 5-phenoxy-1-[3-(trifluoromethyl)phenyl]-1H-tetrazole;

UBH-509; D-489; LS 82-556; KPP-300; KPP-421, MT-146, NC-324; butenachlor (KH-218); DPX-N8189; haloxyfop-etotyl (DOWCO-535); DK-8910; flumioxazin (V-53482); PP-600; MBH-001, amicarbazone, aminopyralid, beflubutamid, benzobicyclon, benzofenap, benzfendizone, butafenacil, chlorfenprop, cloprop, daimuron, dichlorprop-P, dimepipeate, dimethenamid-P, fentrazamide, flamprop-M, fluazolate, indanofan, isoxachlortole, isoxaflutole, MCPA-thioethyl, mecoprop-P, mesotrione, metamifop, penoxsulam, pethoxamid, picolinafen, profluazol, profoxydim, pyraclonil, pyrazolynate, pyridafol, pyriftalid, sulcotrione, thidiazuron.

Suitable safeners are, for example, the following groups of compounds:

1) Compounds of the type of dichlorophenylpyrazoline-3-carboxylic acid (S1), preferably compounds such as ethyl 1-(2,4-dichlorophenyl)-5-(ethoxycarbonyl)-5-methyl-2-pyrazoline-3-carboxylate (S1-1, mefenpyr-diethyl, PM pp. 781-782), and related compounds, as described in WO 91/07874.
2) Derivatives of dichlorophenylpyrazolecarboxylic acid, preferably compounds such as ethyl 1-(2,4-dichlorophenyl)-5-methylpyrazole-3-carboxylate (S1-2), ethyl 1-(2,4-dichlorophenyl)-5-isopropyl-pyrazole-3-carboxylate (S1-3), ethyl 1-(2,4-dichlorophenyl)-5-(1,1-dimethylethyl)pyrazole-3-carboxylate (S1-4), ethyl 1-(2,4-dichlorophenyl)-5-phenylpyrazole-3-carboxylate (S1-5) and related compounds, as described in EP-A-333 131 and EP-A-269 806.
3) Compounds of the type of the triazolecarboxylic acids (S1), preferably compounds such as fenchlorazole, i.e. ethyl 1-(2,4-dichlorophenyl)-5-trichloromethyl-(1H)-1,2,4-triazole-3-carboxylate (S1-6, fenchlorazole-ethyl, PM pp. 385-386), and related compounds (see EP-A-174 562 and EP-A-346 620).
4) Compounds of the type of 5-benzyl- or 5-phenyl-2-isoxazoline-3-carboxylic acid, or 5,5-diphenyl-2-isoxazoline-3-carboxylic acid, preferably compounds such as ethyl 5-(2,4-dichlorobenzyl)-2-isoxazoline-3-carboxylate (S1-7) or ethyl 5-phenyl-2-isoxazoline-3-carboxylate (S1-8) and related compounds, as described in WO 91/08202, or ethyl 5,5-diphenyl-2-isoxazolinecarboxylate (S1-9, isoxadifen-ethyl) or n-propyl ester (S1-10) or ethyl 5-(4-fluorophenyl)-5-phenyl-2-isoxazoline-3-carboxylate (S1-11), as described in the patent application (WO-A-95/07897).
5) Compounds of the type of 8-quinolineoxyacetic acid (S2), preferably 1-methylhex-1-yl (5-chloro-8-quinolineoxy)acetate (S2-1, cloquintocet-mexyl, PM pp. 263-264), 1,3-dimethylbut-1-yl (5-chloro-8-quinolineoxy)acetate (S2-2), 4-allyloxybutyl (5-chloro-8-quinolineoxy)acetate (S2-3), 1-allyloxyprop-2-yl (5-chloro-8-quinolineoxy)acetate (S2-4), ethyl (5-chloro-8-quinolineoxy)acetate (S2-5), methyl (5-chloro-8-quinolineoxy)acetate (S2-6), allyl (5-chloro-8-quinolineoxy)acetate (S2-7), 2-(2-propylideneiminooxy)-1-ethyl (5-chloro-8-quinolineoxy)acetate (S2-8),
2-oxoprop-1-yl (5-chloro-8-quinolineoxy)acetate (S2-9) and related compounds, as described in EP-A-86 750, EP-A-94 349 and EP-A-191 736 or EP-A-0 492 366.
6) Compounds of the type of (5-chloro-8-quinolineoxy)malonic acid, preferably compounds such as diethyl (5-chloro-8-quinolineoxy)malonate, diallyl (5-chloro-8-quinolineoxy)malonate, methyl ethyl (5-chloro-8-quinolineoxy)malonate and related compounds, as described in EP-A-0 582 198.
7) Active compounds of the type of the phenoxyacetic or -propionic acid derivatives or the aromatic carboxylic acids, such as, for example, 2,4-dichlorophenoxyacetic acid (esters) (2,4-D), 4-chloro-2-methylphenoxypropionic esters (mecoprop), MCPA or 3,6-dichloro-2-methoxybenzoic acid (esters) (dicamba).
8) Active compounds of the type of the pyrimidines, such as "fenclorim" (PM, pp. 512-511) (=4,6-dichloro-2-phenylpyrimidine).
9) Active compounds of the type of the dichloroacetamides, which are frequently used as pre-emergence safeners (soil-acting safeners), such as, for example, "dichlormid" (PM, pp. 363-364) (=N,N-diallyl-2,2-dichloroacetamide), "R-29148" (=3-dichloroacetyl-2,2,5-trimethyl-1,3-oxazolidone from Stauffer),
"benoxacor" (PM, pp. 102-103) (=4-dichloroacetyl-3,4-dihydro-3-methyl-2H-1,4-benzoxazine),
"PPG-1292" (=N-allyl-N-[(1,3-dioxolan-2-yl)methyl]dichloroacetamide from PPG Industries),
"DK-24" (=N-allyl-N—[(allylaminocarbonyl)methyl]dichloroacetamide from Sagro-Chem),
"AD-67" or "MON 4660" (=3-dichloroacetyl-1-oxa-3-azaspiro[4,5]decane from Nitrokemia or Monsanto),
"dicyclonon" or "BAS145138" or "LAB145138" (=(=3-dichloroacetyl-2,5,5-trimethyl-1,3-diazabicyclo[4.3.0]nonane from BASF) and
"furilazole" or "MON 13900" (see PM, 637-638) (=(RS)-3-dichloroacetyl-5-(2-furyl)-2,2-dimethyloxazolidone).

10) Active compounds of the type of the dichloroacetone derivatives, such as, for example,
"MG 191" (CAS Reg. No. 96420-72-3) (=2-dichloromethyl-2-methyl-1,3-dioxolane from Nitrokemia).
11) Active compounds of the type of the oxyimino compounds, which are known as seed dressings, such as, for example,
"oxabetrinil" (PM, pp. 902-903) (=(Z)-1,3-dioxolan-2-ylmethoxyimino(phenyl)acetonitrile), which is known as seed dressing safener against metolachlor damage,
"fluxofenim" (PM, pp. 613-614) (=1-(4-chlorophenyl)-2,2,2-trifluoro-1-ethanone O-(1,3-dioxolan-2-ylmethyl) oxime which is known as seed dressing safener against metolachlor damage, and
"cyometrinil" or "CGA-43089" (PM, p. 1304) (=(Z)-cyanomethoxyimino(phenyl)acetonitrile), which is known as seed dressing safener against metolachlor damage.
12) Active compounds of the type of the thiazolecarboxylic esters, which are known as seed dressings, such as, for example,
"flurazole" (PM, pp. 590-591) (=benzyl 2-chloro-4-trifluoromethyl-1,3-thiazole-5-carboxylate), which is known as seed dressing safener against alachlor and metolachlor damage.
13) Active compounds of the type of the naphthalenedicarboxylic acid derivatives, which are known as seed dressings, such as, for example,
"naphthalic anhydride" (PM, p. 1342) (=1,8-naphthalenedicarboxylic anhydride), which is known as seed dressing safener for corn against thiocarbamate herbicide damage.
14) Active compounds of the type of the chromanacetic acid derivatives, such as, for example,
"CL 304415" (CAS Reg. No. 31541-57-8) (=2-84-carboxychroman-4-yl)acetic acid from American Cyanamid).
15) Active compounds which, in addition to a herbicidal action against weed plants, also have safener action on crop plants such as, for example,
"dimepiperate" or "MY-93" (PM, pp. 404-405) (=S-1-methyl-1-phenylethyl piperidine-1-thiocarboxylate),
"daimuron" or "SK 23" (PM, p. 330) (=1-(1-methyl-1-phenylethyl)-3-p-tolylurea),
"cumyluron"="JC-940" (=3-(2-chlorophenylmethyl)-1-(1-methyl-1-phenylethyl)urea, see JP-A-60087254),
"methoxyphenone" or "NK 049" (=3,3'-dimethyl-4-methoxybenzophenone),
"CSB" (=1-bromo-4-(chloromethylsulfonyl)benzene) (CAS Reg. No. 54091-06-4 from Kumiai).

16) Compounds of the type of the acylsulfamoylbenzoamides, for example of the formula (VIII) below, which are known, for example, from WO 99/16744.

(VIII)

| Compound No. | $R^{21}$ | $R^{22}$ |
|---|---|---|
| S3-1 | cyclopropyl | 2-OCH$_3$ |
| S3-2 | cyclopropyl | 2-OCH$_3$, 5-Cl |
| S3-3 | ethyl | 2-OCH$_3$ |
| S3-4 | isopropyl | 2-OCH$_3$, 5-Cl |
| S3-5 | isopropyl | 2-OCH$_3$ |

Preferred safeners are mefenpyr, fenchlorazole, isoxadifen, cloquintocet and their $C_1$-$C_{10}$ alkyl esters, in particular mefenpyr-diethyl (S1-1), fenchlorazole-ethyl (S1-6), isoxadifen-ethyl (S1-9), cloquintocet-mexyl (S2-1), and (S3-1).

The typical auxiliaries and additives f) optionally present in the liquid formulations of the invention are known in principle and are described for example in standard works: McCutcheon's "Detergents and Emulsifiers Annual", MC Publ. Corp., Ridgewood N.J.; Sisley and Wood, "Encyclopedia of Surface active Agents", Chem. Publ. Co. Inc., N.Y. 1964; Schönfeldt, "Grenzflächenaktive Äthylenoxidaddukte", Wiss. Verlagsgesellschaft, Stuttgart 1976; Winnacker-Küchler, "Chemische Technologie", volume 7, C. Hauser-Verlag, Munich, 4th edition 1986.

Examples of typical auxiliaries and additives F) that may also be present in the formulations of the invention are as follows: thixotropic agents, wetting agents, antidrift agents, stickers, penetrants, preservatives, and frost preventatives, antioxidants, fillers, carriers, colorants, odorants, defoamers, fertilizers, evaporation inhibitors, pH modifiers and viscosity modifiers, and also agents which have a positive influence on the stability, particularly the stability toward hydrolysis.

Suitable frost preventatives are those from the group of the ureas, diols, and polyols, such as ethylene glycol and propylene glycol. Suitable defoamers are those based on silicones. Suitable structuring compounds are those from the group of the xanthanes. Suitable preservatives, colorants, and fragrances are known to the skilled worker.

Particularly preferred embodiments are those liquid formulations comprising
A) pyrasulfotole (A-5), pyrasulfotole sodium salt (A-5Na), pyrasulfotole potassium salt (A-5K),
B) bis-2-ethylhexyl sulfosuccinate sodium (B-1),
C) Emulsogen® EL 400 (C-1), Genapol® X-060 (C-2), Genapol® X-150 (C-3),
D) Solvesso® 100 (D-1), Solvesso® 200 ND (D-2),
E) mefenpyr-diethyl (E-1), fenoxaprop-P-ethyl (E-2), bromoxynil (E-3)

Especially preferred embodiments are those liquid formulations comprising the following components:

| | | |
|---|---|---|
| A-5 + B-1 + C-1 + D-1, | A-5 + B-1 + C-2 + D-1, | A-5 + B-1 + C-3 + D-1, |
| A-5Na + B-1 + C-1 + D-1, | A-5Na + B-1 + C-2 + D-1, | A-5Na + B-1 + C-3 + D-1, |
| A-5K + B-1 + C-1 + D-1, | A-5K + B-1 + C-2 + D-1, | A-5K + B-1 + C-3 + D-1, |
| A-5 + B-1 + C-1 + D-2, | A-5 + B-1 + C-2 + D-2, | A-5 + B-1 + C-3 + D-2, |
| A-5Na + B-1 + C-1 + D-2, | A-5Na + B-1 + C-2 + D-2, | A-5Na + B-1 + C-3 + D-2, |
| A-5K + B-1 + C-1 + D-2, | A-5K + B-1 + C-2 + D-2, | A-5K + B-1 + C-3 + D-2, |
| A-5 + B-1 + C-1 + D-1 + E-1, | | A-5 + B-1 + C-2 + D-1 + E-1, |
| A-5 + B-1 + C-3 + D-1 + E-1, | | A-5Na + B-1 + C-1 + D-1 + E-1, |
| A-5Na + B-1 + C-2 + D-1 + E-1, | | A-5Na + B-1 + C-3 + D-1 + E-1, |
| A-5K + B-1 + C-1 + D-1 + E-1, | | A-5K + B-1 + C-2 + D-1 + E-1, |
| A-5K + B-1 + C-3 + D-1 + E-1, | | A-5 + B-1 + C-1 + D-2 + E-1, |
| A-5 + B-1 + C-2 + D-2 + E-1, | | A-5 + B-1 + C-3 + D-2 + E-1, |
| A-5Na + B-1 + C-1 + D-2 + E-1, | | A-5Na + B-1 + C-2 + D-2 + E-1, |
| A-5Na + B-1 + C-3 + D-2 + E-1, | | A-5K + B-1 + C-1 + D-2 + E-1, |
| A-5K + B-1 + C-2 + D-2 + E-1, | | A-5K + B-1 + C-3 + D-2 + E-1, |
| A-5 + B-1 + C-1 + D-1 + E-2, | | A-5 + B-1 + C-2 + D-1 + E-2, |
| A-5 + B-1 + C-3 + D-1 + E-2, | | A-5Na + B-1 + C-1 + D-1 + E-2, |
| A-5Na + B-1 + C-2 + D-1 + E-2, | | A-5Na + B-1 + C-3 + D-1 + E-2, |
| A-5K + B-1 + C-1 + D-1 + E-2, | | A-5K + B-1 + C-2 + D-1 + E-2, |
| A-5K + B-1 + C-3 + D-1 + E-2, | | A-5 + B-1 + C-1 + D-2 + E-2, |
| A-5 + B-1 + C-2 + D-2 + E-2, | | A-5 + B-1 + C-3 + D-2 + E-2, |
| A-5Na + B-1 + C-1 + D-2 + E-2, | | A-5Na + B-1 + C-2 + D-2 + E-2, |
| A-5Na + B-1 + C-3 + D-2 + E-2, | | A-5K + B-1 + C-1 + D-2 + E-2, |
| A-5K + B-1 + C-2 + D-2 + E-2, | | A-5K + B-1 + C-3 + D-2 + E-2, |
| A-5 + B-1 + C-1 + D-1 + E-3, | | A-5 + B-1 + C-2 + D-1 + E-3, |
| A-5 + B-1 + C-3 + D-1 + E-3, | | A-5Na + B-1 + C-1 + D-1 + E-3, |
| A-5Na + B-1 + C-2 + D-1 + E-3, | | A-5Na + B-1 + C-3 + D-1 + E-3, |
| A-5K + B-1 + C-1 + D-1 + E-3, | | A-5K + B-1 + C-2 + D-1 + E-3, |
| A-5K + B-1 + C-3 + D-1 + E-3, | | A-5 + B-1 + C-1 + D-2 + E-3, |
| A-5 + B-1 + C-2 + D-2 + E-3, | | A-5 + B-1 + C-3 + D-2 + E-3, |
| A-5Na + B-1 + C-1 + D-2 + E-3, | | A-5Na + B-1 + C-2 + D-2 + E-3, |
| A-5Na + B-1 + C-3 + D-2 + E-3, | | A-5K + B-1 + C-1 + D-2 + E-3, |
| A-5K + B-1 + C-2 + D-2 + E-3, | | A-5K + B-1 + C-3 + D-2 + E-3, |
| A-5 + B-1 + C-1 + D-1 + E-1 + E-2, | | A-5 + B-1 + C-2 + D-1 + E-1 + E-2, |
| A-5 + B-1 + C-3 + D-1 + E-1 + E-2, | | A-5Na + B-1 + C-1 + D-1 + E-1 + E-2, |
| A-5Na + B-1 + C-2 + D-1 + E-1 + E-2, | | A-5Na + B-1 + C-3 + D-1 + E-1 + E-2, |
| A-5K + B-1 + C-1 + D-1 + E-1 + E-2, | | A-5K + B-1 + C-2 + D-1 + E-1 + E-2, |
| A-5K + B-1 + C-3 + D-1 + E-1 + E-2, | | A-5 + B-1 + C-1 + D-2 + E-1 + E-2, |
| A-5 + B-1 + C-2 + D-2 + E-1 + E-2, | | A-5 + B-1 + C-3 + D-2 + E-1 + E-2, |
| A-5Na + B-1 + C-1 + D-2 + E-1 + E-2, | | A-5Na + B-1 + C-2 + D-2 + E-1 + E-2, |
| A-5Na + B-1 + C-3 + D-2 + E-1 + E-2, | | A-5K + B-1 + C-1 + D-2 + E-1 + E-2, |
| A-5K + B-1 + C-2 + D-2 + E-1 + E-2, | | A-5K + B-1 + C-3 + D-2 + E-1 + E-2, |

-continued

A-5 + B-1 + C-1 + D-1 + E-1 + E-3,
A-5 + B-1 + C-3 + D-1 + E-1 + E-3,
A-5Na + B-1 + C-2 + D-1 + E-1 + E-3,
A-5K + B-1 + C-1 + D-1 + E-1 + E-3,
A-5K + B-1 + C-3 + D-1 + E-1 + E-3,
A-5 + B-1 + C-2 + D-2 + E-1 + E-3,
A-5Na + B-1 + C-1 + D-2 + E-1 + E-3,
A-5Na + B-1 + C-3 + D-2 + E-1 + E-3,
A-5K + B-1 + C-2 + D-2 + E-1 + E-3,
A-5 + B-1 + C-1 + D-1 + E-1 + E-2 + E-3,
A-5 + B-1 + C-2 + D-1 + E-1 + E-2 + E-3,
A-5 + B-1 + C-3 + D-1 + E-1 + E-2 + E-3,
A-5Na + B-1 + C-1 + D-1 + E-1 + E-2 + E-3,
A-5Na + B-1 + C-2 + D-1 + E-1 + E-2 + E-3,
A-5Na + B-1 + C-3 + D-1 + E-1 + E-2 + E-3,
A-5K + B-1 + C-1 + D-1 + E-1 + E-2 + E-3,
A-5K + B-1 + C-2 + D-1 + E-1 + E-2 + E-3,
A-5K + B-1 + C-3 + D-1 + E-1 + E-2 + E-3,
A-5 + B-1 + C-1 + D-2 + E-1 + E-2 + E-3,
A-5 + B-1 + C-2 + D-2 + E-1 + E-2 + E-3,
A-5 + B-1 + C-3 + D-2 + E-1 + E-2 + E-3,
A-5Na + B-1 + C-1 + D-2 + E-1 + E-2 + E-3,
A-5Na + B-1 + C-2 + D-2 + E-1 + E-2 + E-3,
A-5Na + B-1 + C-3 + D-2 + E-1 + E-2 + E-3,
A-5K + B-1 + C-1 + D-2 + E-1 + E-2 + E-3,
A-5K + B-1 + C-2 + D-2 + E-1 + E-2 + E-3,
and
A-5K + B-1 + C-3 + D-2 + E-1 + E-2 + E-3.

A-5 + B-1 + C-2 + D-1 + E-1 + E-3,
A-5Na + B-1 + C-1 + D-1 + E-1 + E-3,
A-5Na + B-1 + C-3 + D-1 + E-1 + E-3,
A-5K + B-1 + C-2 + D-1 + E-1 + E-3,
A-5 + B-1 + C-1 + D-2 + E-1 + E-3,
A-5 + B-1 + C-3 + D-2 + E-1 + E-3,
A-5Na + B-1 + C-2 + D-2 + E-1 + E-3,
A-5K + B-1 + C-1 + D-2 + E-1 + E-3,
A-5K + B-1 + C-3 + D-2 + E-1 + E-3,

Bromoxynil can be used in each case in the form of its potassium salt, heptanoate or octanoate.

The liquid formulations of the invention can be produced by means of customary methods that are already known, as for example by the mixing of the various components by means of stirrers, shakers, mills or (static) mixers. In these cases brief heating of the mixtures may be advantageous in order to obtain complete dissolution of all of the components involved.

The liquid formulations of the invention display a significantly improved application behavior, which is manifested in significantly reduced sieve residues and/or instances of sieve or nozzle clogging. The application rate of the formulations of the invention per hectare varies in general between 0.5 and 5 liters, preferably between 1.0 and 4.0 liters.

For application, the formulations of the invention can be diluted in a conventional way, to form suspensions, emulsions, suspoemulsions or solutions, for example, preferably emulsions, by means, for example, of water. It can be advantageous to admix resulting spray liquors with further agrochemical actives (e.g., tank mix partners in the form of corresponding formulations) and/or auxiliaries and additives that are typical for application, examples being self-emulsifying oils such as vegetable oils or liquid paraffins and/or fertilizers. The present invention thus also provides the herbicidal compositions produced in such a way.

The ratio of inventive formulation to water is typically 1:500 to 1:50. The spray liquor per hectare is typically 50 to 500 liters, preferably 75 to 350 liters of water. In certain cases it is also possible to go above or below the limits indicated here. The formulations are also suitable for aircraft application. For that purpose, inventive formulations are delivered either neat or diluted with water or with organic solvents. The volume of additional carrier liquid in this case varies in general from 0.5 to 50 liters per hectare. The present invention thus also provides herbicidal compositions based on the liquid formulations of the invention.

The herbicidal compositions or formulations of the invention exhibit excellent herbicidal activity against a broad spectrum of economically important monocotyledonous and dicotyledonous weed plants. Even difficult-to-control perennial weeds which produce shoots from rhizomes, rootstocks or other perennial organs are effectively covered. These herbicidal compositions may be applied, for example, prior to sowing, pre-emergence or post-emergence. By way of example a number of representatives may be listed among the monocotyledonous and dicotyledonous weed flora which can be controlled by the herbicidal compositions of the invention, without such naming being intended to constitute any restriction to particular species. Among the monocot weed species those controlled effectively include, for example, *Apera spica venti*, *Avena* spp., *Alopecurus* spp., *Brachiaria* spp., *Digitaria* spp., *Lolium* spp., *Echinochloa* spp., *Panicum* spp., *Phalaris* spp., *Poa* spp., *Setaria* spp., and *Bromus* spp. such as *Bromus catharticus*, *Bromus secalinus*, *Bromus erectus*, *Bromus tectorum*, and *Bromus japonicus*, and *Cyperus* species, from the annual group, and, among the perennial species, *Agropyron*, *Cynodon*, *Imperata*, and *Sorghum*, and also perennial *Cyperus* species. In the case of dicot weed species, the spectrum of action extends to species such as, for example, *Abutilon* spp., *Amaranthus* spp., *Chenopodium* spp., *Chrysanthemum* spp., *Galium* spp. such as *Galium aparine*, *Ipomoea* spp., *Kochia* spp., *Lamium* spp., *Matricaria* spp., *Pharbitis* spp., *Polygonum* spp., *Sida* spp., *Sinapis* spp., *Solanum* spp., *Stellaria* spp., *Veronica* spp., and *Viola* spp., *Xanthium* spp., among the annuals, and also *Convolvulus*, *Cirsium*, *Rumex* and *Artemisia* among the perennial weeds. Weed plants which occur in rice under the specific culture conditions, such as *Echinochloa*, *Sagittaria*, *Alisma*, *Eleocharis*, *Scirpus*, and *Cyperus*, are likewise controlled to outstanding effect by the compositions of the invention.

Where the herbicidal compositions of the invention are applied to the soil surface prior to germination, then either emergence of the weed seedlings is prevented completely, or the weeds grow until they have reached the cotyledon stage, but their growth then comes to a standstill and, after three to four weeks have elapsed, they die off completely.

When the herbicidal compositions of the invention are applied post-emergence to the green parts of plants there is likewise a drastic arrest in growth very soon after the treatment, and the weeds remain at the growth stage they were in at the time of application, or die off completely after a certain time, so that in this way competition by the weeds, which is detrimental to the crop plants, is eliminated at a very early stage and in a sustained manner.

The herbicidal compositions of the invention are notable for a herbicidal action with a fast onset and long duration. The rain resistance of the active ingredients in the inventive combinations is generally favorable. A particular advantage is that the levels of herbicidal compounds that are active and are used in the herbicidal compositions can be made so low that their soil effect is at an optimally low level. Hence not only does it become possible to use them in sensitive crops, but also groundwater contamination is almost completely ruled out. The inventive combination of active ingredients allows a considerable reduction in the required application rate of the active ingredients.

The stated properties and advantages are beneficial in practical weed control in order to keep agricultural crops free of unwanted competitor plants and hence to secure and/or increase the yields in terms of quality and quantity. With regard to the properties described, these new compositions significantly surpass the technical standard.

Although the herbicidal compositions display excellent herbicidal activity against monocot and dicot weeds, crop plants of economic importance, examples being dicotyledonous crops such as soybean, cotton, oilseed rape, sugar beet, or gramineous crops such as wheat, barley, rye, oats, millet, rice or maize, are damaged either only to an insignificant extent or not at all. For these reasons the herbicidal compositions of the invention are especially suitable for the selective control of unwanted plant growth in stands of agricultural crop plants or ornamentals.

Furthermore, the herbicidal compositions of the invention exhibit outstanding growth regulator properties in crop plants. They exert regulatory intervention in the plants' own metabolism and can therefore be employed to exert a controlled influence on plant constituents and to facilitate harvesting, such as by initiating desiccation and stunting of growth, for example. They are also suitable, moreover, for the general control and inhibition of unwanted vegetative growth, without killing off the plants. The inhibition of vegetative growth plays an important part in numerous monocot and dicot crops, since it allows lodging to be reduced or prevented completely.

On the basis of their herbicidal and plant growth regulator properties, the herbicidal compositions of the invention can also be used for controlling weed plants in crops of genetically modified plants which are known or are yet to be developed. As a general rule the transgenic plants are distinguished by particular advantageous properties, such as by resistance to certain pesticides, especially certain herbicides, resistance to plant diseases or plant-disease pathogens, such as certain, insects or microorganisms such as fungi, bacteria or viruses. Other particular properties relate for example to the harvested material, in terms of quantity, quality, storage properties, composition, and specific constituents. For instance, transgenic plants are known which feature increased starch content or modified quality of starch, or whose fatty acid composition in the harvested material is different.

Preference is given to the use of the herbicidal compositions of the invention in economically significant transgenic cultures of crop plants and ornamentals, such as of gramineous cultures such as wheat, barley, rye, oats, millet, rice, and maize, or else crops of sugar beet, cotton, soybeans, oilseed rape, potato, tomato, pea, and other vegetables. The compositions of the invention can be used with preference in crops which are resistant or have been made genetically resistant to the phytotoxic effects of the herbicides.

When the herbicidal compositions of the invention are employed in transgenic crops, effects are frequently apparent—in addition to the effects on weed plants that are observed in other crops—that are specific to application in the particular transgenic crop: for example, a modified or specifically widened controllable weed spectrum, modified application rates which can be used for application, preferably effective capacity for combination with the herbicides ingredients to which the transgenic crop is resistant, and also influencing of growth and yield of the transgenic crop plants.

The present invention hence further provides a method of controlling unwanted plant growth, preferably in plant crops such as cereals (e.g., wheat, barley, rye, oats, rice, maize, millet), sugar beet, sugarcane, oilseed rape, cotton, and soybeans, more preferably in monocotyledonous crops such as cereals, e.g., wheat, barley, rye, oats, hybrids thereof, such as triticale, rice, maize, and millet, which comprises applying one or more herbicidal compositions of the invention to the weed plants, plant parts, plant seeds or the area on which the plants are growing, e.g., the area under cultivation.

The plant crops can also be genetically modified or a product of mutation selection, and are preferably tolerant toward acetolactate synthase (ALS) inhibitors.

Emulsifiable concentrates are prepared, for example, by dissolving the active A) or the actives A) and E) in one or more solvents D) with addition of dialkyl sulfosuccinate B) and surfactant C) and also, where appropriate, of further auxiliaries and additives F).

WORKING EXAMPLES

The terms used in the following examples have the following definitions:

| | |
|---|---|
| Emulsogen ® EL 400 = | ethoxylated caster oil with 40 ethyleneoxy units |
| Genapol ® X-060 = | nonionic surfactant based on ethoxylated isotridecanol polyglycol ether |
| Genapol ® X-150 = | nonionic surfactant based on ethoxylated isotridecanol polyglycol ether |

Preparation of Emulsifiable Concentrates

The mode of preparation described below refers to the formulas of examples 1 to 4 below:

Component A) and component B) are stirred together in a stirring vessel to give a dispersion, which is then heated to approximately 80° C. When component A) has dissolved, components D), C), and E) are added with stirring.

Example 1

A) 3.50 g pyrasulfotole potassium salt (A-5K)

B) 30.00 g bis-2-ethylhexyl sulfosuccinate sodium as a 64% strength solution in Solvesso® 100 (B-1), C) 9.50 g Emulsogen® EL 400 (C-1), D) 57.00 g Solvesso® 200 ND (D-2).

Example 2

A) 3.50 g pyrasulfotole potassium salt (A-5K)
B) 30.00 g bis-2-ethylhexyl sulfosuccinate sodium as a 64% strength solution in Solvesso® 100 (B-1),
C) 7.50 g Emulsogen® EL 400 (C-1),
C) 7.50 g Genapol® X-150 (C-3),
D) 42.00 g Solvesso® 200 ND (D-2),
E) 2.70 g mefenpyr-diethyl (E-1)
E) 6.80 g fenoxaprop-P-ethyl (E-2).

Example 3

A) 3.50 g pyrasulfotole potassium salt (A-5K)
B) 30.00 g bis-2-ethylhexyl sulfosuccinate sodium as a 64% strength solution in Solvesso® 100 (B-1),
C) 7.30 g Emulsogen® EL 400 (C-1),
C) 11.50 g Genapol® X-060 (C-2),
D) 45.00 g Solvesso® 200 ND (D-2),
E) 2.70 g mefenpyr-diethyl (E-1)

Example 4

A) 3.50 g pyrasulfotole potassium salt (A-5K)
B) 30.00 g bis-2-ethylhexyl sulfosuccinate sodium as a 64% strength solution in Solvesso® 100 (B-1),
C) 5.00 g Emulsogen® EL 400 (C-1),
C) 15.00 g Genapol® X-150 (C-3),
D) 37.00 g Solvesso® 200 ND (D-2),
E) 2.70 g mefenpyr-diethyl (E-1)
E) 6.80 g fenoxaprop-P-ethyl (E2).

The emulsifiable concentrates of the invention that are obtained in this way are chemically stable and even after prolonged storage remain clear and homogenous, and can be diluted with water to give a homogeneous emulsion.

Comparative Example

For purposes of comparison
A) 3.50 g pyrasulfotole potassium salt (A-5K)
C) 7.30 g Emulsogen® EL 400 (C-1),
C) 11.50 g Genapol® X-060 (C-3),
D) 75.00 g Solvesso® 200 ND (D-2) and
E) 2.70 g mefenpyr-diethyl (E-1)
but without component B) are stirred together under the conditions stated above. In contrast to the working examples according to the invention, no clear homogeneous solution is formed.

The invention claimed is:

1. A liquid formulation comprising
A) 0.1% to 50% of a HPPD inhibitor selected from the group consisting of pyrasulfotole, toprarnezone, and salts thereof,

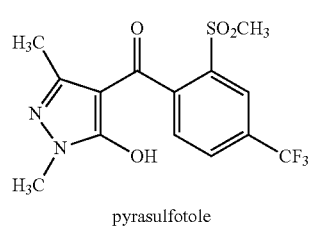

pyrasulfotole

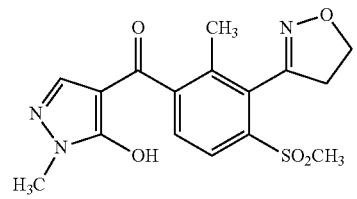

topramezone

B) 1% to 50% of a dialkyl sulfosuccinate selected from the group consisting of sodium diisooctyl sulfosuccinate, sodium di(2-ethylhexyl) sulfosuccinate, disodium alcohol polyethylene glycol ether semisulfosuccinate, disodium N-alkylsulfosuccinamate, disodium fatty acid amide polyethylene glycol ether sulfosuccinate, and tetrasodium N-(1,2-dicarboxyethyl)-N-octadecyl-sulfosuccinamate, C) 2% to 40% of a surfactant selected from the group consisting of (1) a nonionic surfactant based on ethoxylated isotridecanol polyglycol ether, (2) a C12/C14 alkyl ether sulphate, and (3) an ethoxylated castor oil, D) 5% to 80% of a solvent selected from the group consisting of aliphatic or aromatic hydrocarbons, ethers, ketones, nitriles and vegetable oils and their transesterification products, E) 0% to 25% of an auxillary and/or additive; and F) 0% to 50% of one or more agrochemical actives other than said A).

2. A process for preparing a liquid formulation as claimed in claim 1, comprising mixing said components A), B), C) and D).

3. A herbicidal composition comprising a liquid formulation as claimed in claim 1.

4. A liquid herbicidal composition obtainable by diluting a liquid formulation as claimed in claim 1.

5. A method for controlling unwanted plant growth comprising applying a liquid formulation of claim 1 to an area on which a plant can grow.

6. A method of controlling unwanted plant growth comprising applying an effective amount of a liquid formulation as claimed in claim 1 to a plant, a part of a plant, a seed or an area on which a plant can grow.

7. The liquid formulation of claim 1, wherein said HPPD inhibitor is pyrasulfotole.

8. The liquid formulation of claim 1, wherein said HPPD inhibitor is toprarnezone.

9. The liquid formulation of claim 1, wherein said HPPD inhibitor is a salt of pyrasulfotole.

10. The liquid formulation of claim 1, wherein said HPPD inhibitor is a salt of toprarnezone.

11. The liquid formulation of claim 1, wherein said HPPD inhibitor is pyrasulfotole potassium salt.

12. The liquid formulation of claim 1, wherein said HPPD inhibitor is toprarnezone sodium or potassium salt.

13. The liquid formulation of claim 1, wherein said HPPD inhibitor is present in an amount from 0.5% to 25%.

14. The liquid formulation of claim 1, wherein said dialkyl sulfosuccinate is present in an amount from 2% to 25%.

15. The liquid formulation of claim 1, wherein said surfactant is present in an amount from 5% to 25%.

16. The liquid formulation of claim 1, wherein said solvent is present in an amount from 10% to 80%.

17. The liquid formulation of claim 1 comprising
E) an auxiliary or additive.

18. The liquid formulation of claim 1 comprising
F) one or more further non-A) agrochemical actives.

* * * * *